United States Patent [19]
Stern et al.

[11] Patent Number: 5,891,709
[45] Date of Patent: Apr. 6, 1999

[54] CAMPY-CEFEX SELECTIVE AND DIFFERENTIAL MEDIUM FOR CAMPYLOBACTER

[75] Inventors: Norman J. Stern, Athens, Ga.; Boleslaw J. Wojton; Kris Kwiatek, both of Pulawy, Poland

[73] Assignee: The United States of America as represented by the Secretary of the Agriculture, Washington, D.C.

[21] Appl. No.: 912,447

[22] Filed: Jul. 13, 1992

[51] Int. Cl.$^6$ .............................. C12N 1/04; C12N 1/12; C12N 1/20

[52] U.S. Cl. .................. 435/252.1; 435/260; 435/287.1; 435/822

[58] Field of Search ................................ 435/252.1, 253, 435/287, 260, 287.1, 822

[56] References Cited

U.S. PATENT DOCUMENTS 4,904,597  2/1990  Inoue et al. ........................... 435/252.1

OTHER PUBLICATIONS

Hutchinson, D N, et al., "Is Enrichment Culture Necessary for the Isolation of *Campylobacter jejuni* from Faeces?", *J. Clin Pathol*, 1983, 36, pp. 1350–1352.

Hutchinson, D N, et al., "Improved Blood Free Selective Medium for the Isolation of *Campylobacter jejuni* from Faecal Specimens," *J. Chem. Pathol.*, 36, 1984, pp. 956–957.

Bolton, F J., et al., "A Selective Medium for isolating *Campylobacter jejuni/coli* ", *J. Clin Pathol*, 1982, 35, pp. 462–467.

Blaser, Martin J., MD, et al., "*Campylobacter enteritis*: Clinical and Epidemiologic Features", *Annals of Internal Medicine*, Aug. 1979, vol. 91, No. 2, pp. 179–185.

Rothenberg, P J, et al., "Selected Enrichment Broths for Recovery of *Campylobacter jejuni* from Foods", *Applied and Environmental Microbiology*, Jul. 1984, vol. 48, No. 1, pp. 78–80.

Hunt, Jan M., "Chapter 7—*Campylobacter*", in:*Food and Drug Administration Bacteriological Analytical Manual*, 7th Edition, 1992, (AOAC International), pp. 77–94.

Difco Laboratories, "Dehydrated Culture Media", *Difco Product Catalog and Reference Guide*, Effective: Jan. 1992, pp. 7–8.

"Campylobacter Agar with 5 Antimicrobics and 10% Sheep Blood", *Manual of BBL Products and Laboratory Procedures*, Sixth Edition, Power, David A., and McCuen, Peggy J., Editors, pp. 126–127 1992.

Smibert, Robert M., "Campylobacter", *Bergey's Manual of Systematic Bacteriology*, vol. 1, (Williams and Wilkins), pp. 111–115 1992.

Abstracts of Papers Presented at the Seventy–Eighth Annual Meeting of the IAMFES, *Journal of Food Protection*, Jul. 21–24, 1991, Louisville, KY, Oct. 1991, pp. 818–819.

*Primary Examiner*—Michael G. Wityshyn
*Assistant Examiner*—Deborah K. Ware
*Attorney, Agent, or Firm*—M. Howard Silverstein; Randall E. Deck; John D. Fado

[57] ABSTRACT

A solid or semi-solid culture medium, designated Campy-Cefex, for the isolation of Campylobacter species. The culture medium includes:

(a) a nutrient medium with an energy source effective to support growth of Campylobacter;

(b) agar;

(c) blood;

(d) a first selective agent selected from cycloheximide, its salts, or mixtures thereof; and (e) a second selective agent selected from cefoperazone, its salts, or mires thereof.

In use, the sample to be analyzed is inoculated onto the Campy-Cefex culture medium, and subsequently incubated for a sufficient time and under conditions effective to promote growth of Campylobacter. Following incubation, the culture medium may then be examined for the presence of any colonies of Campylobacter.

8 Claims, No Drawings

CAMPY-CEFEX SELECTIVE AND DIFFERENTIAL MEDIUM FOR CAMPYLOBACTER

BACKGROUND OF THE INVENTION

1. Field of Invention

This invention relates to an improved medium for the selective and differential culture of Campylobacter species, especially C. jejuni and C. coli.

2. Description of the Prior Art

Campylobacter jejuni, C. coli and C. laridis are known to cause an estimated 2.2 million cases of foodborne gastroenteritis per year in the United States alone (Tauxe et al., 1987, Am. J. Public Health, 77:1219–1221). The vast majority of these cases are associated with the consumption of improperly prepared poultry or foods and hands cross-contaminated by raw poultry. Although the origin of this disease in humans is primarily linked to poultry, the food microbiology and poultry communities have been slow in directing substantive attention toward the organism. In part, this has been due to the unique physiological requirements of these organisms, impairing their culture and identification from foods and clinical specimens.

A variety of enrichment and culture media have been proposed for the isolation of Campylobacter species [Park et al, Campylobacter, In: *Compendium of Methods for the Microbiological Examination of Foods*, second edit., M. L. Speck (ed.), Am. Pub. Hlth. Assoc., Washington, D.C., 1984, p. 386–404, the contents of which are incorporated by reference herein]. Because Campylobacter can be overgrown by other organisms present in sect sources, the use of selective media, incorporating antibiotics and/or antimicrobial agents, is essential for their culture. Ideally, any culture medium selected should also be differential, allowing the characterization of the Campylobacter by distinctive colonial appearances in culture.

Butzler developed a selective medium for C. jejuni containing a nutrient agar base, blood, and five selective agents, cycloheximide, cefazolin, bacitracin, colistin sulfate and novobiocin, as described by Smibert [Canpylobaceer, In: *Bergey's Manual of Systematic Bacteriology*, Vol. 1, Krieg and Holt (ed.), Williams and Wilkins, Baltimore, Md., 1984, pages 111–115, the contents of which are incorporated by reference herein]. Other selective media that have been developed include: Preston medium (Hut hinson and Bolton, J. Clin. Pathol., 1983, 36:1350–1352) containing nutrient broth, agar, lysed horse blood, cyclohemimide, polymyxin sulphate, trimethoprim lactate and rifampicin; Skirrow's medium (Skirrow, Br. Med. J., 1977, ii:9–11) containing a nutrient agar base, lysed horse blood, vancomycin, polymyxin and trimethoprim; and Camipy-BAP (Blaser et al., 1979, Ann. Intern. Med., 91:179–185) containing brucella agar, sheep erythrocytes, vanoocycin, trimethoprim, polymyxin B, cephalothin, and amphotericin B. While all of these media offer some selectivity, the degree of this selectivity has been limited, and the growth of some strains of Campylobacter may be inhibited as well.

One agar medium in particular, CCDA, has gained prominence for the isolation of Campylobacter. Early formulations of CCDA (Hutchinson and Bolton, 1983, J. Clin. Pathol., 36:1350–1352) contained nutrient broth, agar, charcoal, casein hydrolysates, ferrous sulfate, sodium pyruvate and, as selective agents, sodium deoxyoholate and cephazolin. In later formulations the cephazolin was replaced with cefoperazone for improved selectivity (Hutchinson and Bolton, 1984, J. Clin. Pathol., 37:956–957). However, colonies of Campylobacter grown on CCDA have been difficult to differentiate from colonies of other containing microorganisms

SUMMARY OF THE INVENTION

We have now discovered an improved solid or semi-solid culture medium, designated Campy-Cefex, for the isolation of Campylobacter species. The culture medium includes:

(a) a nutrient medium with an energy source effective to support growth of Campylobacter;

(b) agar;

(c) blood;

(d) a first selective agent selected from cycloheximide, its salts, or mixtures thereof; and (e) a second selective agent selected from cefoperazone, its salts, or mixtures thereof.

In use, the sample to be analyzed is inoculated onto the Campy-Cefex culture medium, and subsequently incubated for a sufficient time and under conditions effective to promote growth of Campylobacter. Following incubation, the culture medium may then be examined for the presence of any colonies of Campylobacter.

In accordance with this discovery, it is an object of this invention to provide an improved culture medium and method for the isolation of Campylobacter species.

A further object of this invention to provide a culture medium which is both selective and differential for the growth of Campylobacter in samples containing a mixed flora of microorganisms.

Other objects and advantages of this invention will become readily apparent from the ensuing description.

DETAILED DESCRIPTION OF THE INVENTION

The Campy-Cefex medium of this invention may be used for the isolation of Campylobacter, particularly C. jejuni and/or C. coli, from a variety of sources. Although the medium is particularly valuable for the growth and recovery of this microorganism from samples taken from poultry carcasses, especially chickens, it is understood that the medium may also be used for the isolation of Campylobacter from any samples suspected of containing this pathogen. Without being limited thereto, other sources include animal carcasses such as cattle and sheep, food, milk, water, or clinical sources such as faces or blood. The culture medium contemplated for use in this invention may be prepared using techniques conventional in the art. The basal medium components, including agar and nutrient medium with an energy source are mixed and sterilized by autoclaving. After cooling the sterilized basal medium to about 50°–55° C., blood and filter-sterilized cycloheximide and cefoperazone are added with mixing, and the medium finally poured into a culture container such as a petri dish or flask and cooled to allow the agar to solidify.

Basal medium components selected for use are not critical and may be readily determined by the practitioner skilled in the art. Any nutrient medium and energy source effective to support growth of Campylobacter, particularly C. jejuni and/or C. coli, may be used. Suitable nutrient media include but are not limited to Brucella agar (e.g. BBL, Cockeysville, Md.; Difco Laboratories, Detroit, Mich.; or CM 691, Oxoid, Columbia, Md.), Campylobacter agar base (Difco), Blood agar base no. 2 (Oxoid), Brain-heart infusion agar (BBL; Difco), or Columbia Blood Agar Base. A variety of energy sources may also be employed, and may be incorporated into commercially available nutrient media or added separately. Suitable energy sources for use in the medium are described by Smibert (in Bergey's Manual, ibid, the contents of which are incorporated by reference herein) and include pyruvate, citrate, succinate, cis-aconitate, isocitrate, α-ketoglutarate, fumarate, malate, and oxaloacetate.

The source of the blood added to the medium also is not critical. While horse blood, and especially lysed horse blood, is preferred, it is understood that other blood sources may be used, such as sheep blood.

As noted hereinabove, Campy-Cefex includes two selective agents to prevent the growth of contaminating microorganisms present in the samples to be tested, but which do not inhibit growth of Campylobacter species. The first selective agent is selected from cycloheximide, its salts, and mixtures thereof. The second selective agent is selected from cefoperazone, its salts, and mixtures thereof. Particularly preferred as the selective agents are the sodium salts of cycloheximide and cefoperazone. Surprisingly, we have discovered that the combination of these two selective agents in Campy-Cefex provides excellent selectivity for Campylobacter without the need for additional antibiotics or antibacterial agents employed by other media conventional in the art as described hereinabove.

Other adjuvants may also be incorporated into Campy-Cefex medium for enhancing growth and/or aerotolerance of Campylobacter. Preferred adjuvants enhancing aerotolerance are described by Smibert (ibid) and include but are not limited to sodium pyruvate, ferrous sulfate, bovine superoxide dismutase, catalase, and reducing agents such as sodium bisulfite or sodium metabisulfite. Particularly preferred for addition to the medium are ferrous sulfate, sodium metabisulfite or sodium bisulfite, and sodium pyruvate (FBP). It is understood that the use of blood in the media also enhances aerotolerance because it contains catalase and superoxide dismutase.

The concentration and amount of each of the components of the Canny-Cefex medium are variable and may be readily determined by the practitioner skilled in the art. The amount of each component of the basal or nutrient media should be effective to promote growth of Campylobacter species, while the amount of the first and second selective agents should be effective to inhibit growth of contaminating (non-Campylobacter) micro-organisms without substantially inhibiting growth of Campylobacter species relative to culture medium lacking these selective agents. Without being limited thereto, preferred ranges of the selective agents include about 20–50 mg of cefoperazone, and about 100–400 mg of cycoheximide per liter of Campy-Cefex medium. In accordance with a particularly preferred formulation of Campy-Cefex, ranges of the amount of each component per liter include but are not limited to:

| | |
|---|---|
| Brucella agar | about 40–50 g |
| lysed horse blood | about 20–100 ml (2–10%) |
| sodium cycloheximide | about 100–400 mg |
| sodium ceforerazone | about 20–50 mg |
| ferrous sulfate | about 0.1–1 g |
| sodium bisulfite | about 0.05–5 g |
| sodium pyruvate | about 0.1–1.0 g, and |
| $dH_2O$ | about 950 ml. |

The final pH of the medium should generally be between about 6.5 to 7.5.

In use, the sample to be analyzed is inoculated onto the culture medium using techniques conventional in the art and is incubated for a sufficient time and under conditions effective to promote growth of Campylobacter, especially *C. jejuni* and/or *C. coli*. Suitable conditions may be readily determined by the practitioner skilled in the art and are described by Smibert (ibid). Without being limited thereto, preferred conditions include a temperature between about 35° to 44° C., especially 42° to 43° C., and a low oxygen tension (i.e. microaerobic), especially an oxygen concentration between 3–6%. Techniques for generating this reduced atmosphere are well known in the art and are described, for example, by Inoue (U.S. Pat. No. 4,904,597), or Hutchinson and Bolton (J. Clin. Pathol., 1983, 36:1350–1352), or Park et al (ibid), the contents of each of which are incorporated by reference herein. In the alternative, a suitable atmosphere may be generated using dry ice placed in a sealed container with the cultures.

Following incubation, generally after about 24 to 72 hours, the culture may be examined for the presence of colonies indicative of Campylobacter. Colonies of Campylobacter on the Campy-Cefex medium of this invention are translucent and grow to approximately 2 to 5 mm in diameter, but may also grow to confluence if the medium is moist. These colonies can be readily discriminated from non-Campylobacter breakthrough flora, which are opaque in appearance. Further confirmatory testing of the colonies and speciation can be conducted as described by Park et al (ibid) or Smibert (ibid).

EXAMPLE 1

The Campy-Cefex medium of this invention was compared with two other culture media, Campy-BAP and a modified CCDA supplemented with cycloheximide, for their ability to isolate Campylobacter species from chicken carcasses.

Media: The composition of Campy-Cefex, modified CCDA and Campy-BAP are provided in Table 1. All media were prepared in our laboratories and used immediately or stored in the dark at 4° C. no more than two weeks prior to use. The basal media components were autoclaved at 121° C. for 15 min. The sterilized agar was then tempered in a waterbath to 50°–55° C., and the lysed horse blood and filter-sterilized antibiotics were added and gently mixed before the plates were poured. Filter-sterilized sodium cycloheximide (200 mg/L) was added as a 10% solution in 50% methanol. One gram of sodium cefoperazone was dissolved in 10 ml of sterile, distilled water. Each ml of this solution provided 100 mg cefoperazone/3 L of Campy-Cefex agar. The unused portion of cefoperazone was held in storage at −20° C.

Sampling: During the first stage of the experiment, 21 poultry carcasses were sampled, employing a carcass swab technique to obtain the carcass-associated microflora. The swab samples were acquired by pre-moistening sterile cotton swabs in Cary-Blair transport medium (Park et al., ibid, the contents of which are incorporated by reference herein) and swabbing a 100 $cm^2$ area in the vicinity of the chicken vent and inner thighs, after evisceration but before chilling of the carcasses. Swabs were put back into the tubes of Cary-Blair and transported on ice to the laboratory within two hours. Each swab was then plated onto each of the three media immediately upon arrival.

The swab samples were used to inoculate the three test media in parallel. After the swab was used to inoculate a corner of one test medium, it was rotated one-third turn to provide uniformity of sample application. The swabbed corner of the plate was streaked for isolation of the representative flora. Plates were assessed for the presence of Campylobacter spp., and non-Campylobacter breakthrough flora, after incubation in a microaerobic atmosphere (5% $O_2$, 10% $CO_2$ and 85% $N_2$) at 42° C. for 48 hours, as previously described (Park et al., ibid). This atmosphere was obtained by flushing the normal atmosphere out of the container with the microaerobic atmosphere. Criteria for presumptive identification were based upon a translucent colonial appearance (on Campy-EAP and Campy-Cefex), microscopic examination for curved to spiral-shaped bacterial rods, and positive catalase and oxidase testing as described by Part et al. (ibid).

In the second stage of the study, two lots of ten, whole raw broiler carcasses were procured from a retail grocer. Each lot was comprised of carcasses produced by three or four different poultry companies. These carcasses were washed by shaking for one minute in large plastic bags containing 200 ml of sterile buffered peptone (pH 7.2) to obtain a representative, carcass-associated microflora. The wash water suspension was centrifuged at 5,000×g for 10 min and the pellet was resuspended in one-ml of buffered peptone. The suspension was swabbed and streaked on the three agar media as described above.

Results: Table 2 contains information comparing the efficiency of Campy-BAP, Campy-fex, and modified CCDA media in isolating Campylobacter spp. from chicken carcasses. Among the total of 41 carcasses tested, the organism was isolated 33 times using Campy-BAP; 37 times using Campy-Cefex; and 35 times using modified CCDA. However, the Campy-BAP medium was not as selective as the other media. Contaminating breakthrough flora occurred consistently on the Campy-BAP medium and less frequently or not at all on the other two media tested. Although the modified CCDA medium exhibited similar selectivity when oared with Campy-Cefex medium, differentiation between Campylobacter colonies and other breakthrough flora was significantly more difficult on modified CCDA medium. The Campy-Cefex medium described herein provides both excellent selectivity and a capacity for differentiating Campylobacter species from breakthrough flora.

It is understood that the foregoing detailed description is given merely by way of illustration and that modifications and variations may be made therein without departing from the spirit and scope of the invention.

TABLE 1

Composition of Agar Media.

Campy-Cefex agar.

Basal medium

| | |
|---|---|
| Brucella agar | 44 g |
| Ferrous sulfate ($FeSO_4 \cdot 7H_2O$) | 0.5 g |
| Sodium bisulfite | 0.2 g |
| Sodium pyruvate | 0.5 g |
| $dH_2O$ | 950 ml |

Supplements

| | |
|---|---|
| Sodium cefoperazone | 33 mg |
| Sodium cycloheximide | 200 mg |
| Lysed horse blood | 50 ml |

Modified CCDA agar.

Basal medium

| | |
|---|---|
| Nutrient broth No. 2 | 25 g |
| Bacteriological charcoal | 4 g |
| Casein hydrolysate | 3 g |
| Sodium desoxycholate | 1 g |
| Ferrous sulfate ($FeSO_4 \cdot 7H_2O$) | 0.25 g |
| Sodium pyruvate | 0.25 g |
| Agar | 12 g |

TABLE 1-continued

Composition of Agar Media.

| | |
|---|---|
| Yeast extract | 2 g |
| $dH_2O$ | 1000 ml |

Supplements

| | |
|---|---|
| Sodium cefoperazone | 30 mg |
| Sodium cycloheximide | 100 mg |

Campy-BAP.

Basal medium

| | |
|---|---|
| Brucella agar | 44 g |
| $dH_2O$ | 950 ml |

Supplements

| | |
|---|---|
| Lysed horse blood | 50 ml |
| Vancomycin | 10 mg |
| Polymyxin B | 2500 IU |
| Trimethoprim lactate | 25 mg |
| Amphotericin B | 2 mg |
| Cephalothin | 15 mg |

TABLE 2

Recovery of Campylobacter spp. (*C. jejuni, C. laridis*) from chicken carcasses by direct plating onto Campy-BAP, Campy-Cefex, and modified CCDA media.

| Medium | Number of Carcasses Examined | Incidence-number of Campylobacter spp. positive carcasses | Contamination by other species Heavy[1] | Slight[2] |
|---|---|---|---|---|
| TRAIL 1 - post evisceration, pre-chilled carcasses | | | | |
| Campy-BAP | 21 | 16 | 4 | 17 |
| Campy-Cefex | 21 | 21 | 0 | 4 |
| Modified CCDA | 21 | 21 | 0 | 3 |
| TRAIL 2 - carcasses procured from retail markets | | | | |
| Campy-BAP | 10 | 7 | 10 | 0 |
| Campy-Cefex | 10 | 7 | 6 | 0 |
| Modified CCDA | 10 | 7 | 3 | 1 |
| TRIAL 3 - carcasses procured from retail markets | | | | |
| Campy-BAP | 10 | 10 | 10 | 0 |
| Campy-Cefex | 10 | 9 | 0 | 2 |
| Modified CCDA | 10 | 7 | 0 | 0 |

[1]less than 10% of the bacterial population on the plate
[2]greater than 10% of the bacterial population on the plate

We claim:

1. A composition for the isolation of Campylobacter species comprising:
   (a) a nutrient medium with an energy source effective to support growth of *Campylobacter jejuni* or *Campylobacter coli* or both;
   (b) agar;
   (c) blood;
   (d) a first selective agent selected from the group consisting of cycloheximide, salts of cycloheximide and mixtures thereof; and
   (e) a second selective agent selected from the group consisting of cefoperazone, salts of cefoperazone, and mixtures thereof;
   and wherein said composition does not include bacitracin, colistin sulfate or novobiocin as selective agents.

2. A composition as described in claim 1 wherein the concentration of said blood is between about 2% to 10%, the concentration of said first selective agent is between about 100 to 400 mg/liter, and the concentration of said second selective agent about 20 to about 50 mg/liter.

3. A composition as described in claim 1 wherein said energy source is selected from the group consisting of pyruvate, citrate, succinate, cis-aconitate, isocitrate, α-ketoglutarate, fumarate, malate, and oxaloacetate.

4. A composition as described in claim 1 which includes ferrous sulfate, a reducing agent, and sodium pyruvate.

5. A composition as described in claim 4 wherein said reducing agent is selected from the group consisting of sodium bisulfite and sodium metabisulfite.

6. A composition as described in claim 1 wherein said blood is selected from the group consisting of horse blood and sheep blood.

7. A composition as described in claim 6 wherein said blood is lysed.

8. A composition for the recovery of Campylobacter species comprising:
   (a) a nutrient medium;
   (b) agar;
   (c) ferrous sulfate;
   (d) a reducing agent selected from the group consisting of sodium metabisulfite and sodium bisulfite;
   (e) pyruvate;
   (f) blood;
   (g) a first selective agent selected from the group consisting of cycloheximide, salts of cycloheximide and mixtures thereof; and
   (h) a second selective agent selected from the group consisting of cefoperazone, salts of cefoperazone, and mixtures thereof;
   and wherein said composition does not include bacitracin, colistin sulfate or novobiocin as selective agents.

* * * * *